United States Patent
Garnier et al.

(10) Patent No.: US 8,945,610 B2
(45) Date of Patent: Feb. 3, 2015

(54) CONDENSATION PRODUCTS BASED ON BICYCLIC OR POLYCYCLIC AROMATICS OR HETEROAROMATICS

(75) Inventors: Sebastien Garnier, Weinheim (DE); Stephan Hüffer, Ludwigshafen (DE); Günter Scherr, Ludwigshafen (DE); Joachim Roser, Mannheim (DE); Ulrich Mrowietz, Kronshagen (DE); Hans Wilhelm Doerr, Dreieich (DE); Jindrich Cinatl, Offenbach (DE); Martin Michaelis, Frankfurt am Main (DE)

(73) Assignee: BASF SE, Ludwigshafen (DE)

( * ) Notice: Subject to any disclaimer, the term of this patent is extended or adjusted under 35 U.S.C. 154(b) by 1030 days.

(21) Appl. No.: 12/742,939

(22) PCT Filed: Nov. 11, 2008

(86) PCT No.: PCT/EP2008/065319
§ 371 (c)(1),
(2), (4) Date: Aug. 31, 2010

(87) PCT Pub. No.: WO2009/062932
PCT Pub. Date: May 22, 2009

(65) Prior Publication Data
US 2010/0316695 A1   Dec. 16, 2010

(30) Foreign Application Priority Data

Nov. 14, 2007   (EP) .................................. 07120669

(51) Int. Cl.
  *A61K 31/785*   (2006.01)
  *A61K 31/765*   (2006.01)
  *A61K 31/795*   (2006.01)
  *C08G 12/12*   (2006.01)
  *C08G 12/32*   (2006.01)
  *C08G 14/06*   (2006.01)
  *C08G 14/08*   (2006.01)
  *C14C 3/20*   (2006.01)

(52) U.S. Cl.
  CPC ............. *A61K 31/765* (2013.01); *A61K 31/795* (2013.01); *C08G 12/12* (2013.01); *C08G 12/32* (2013.01); *C08G 14/06* (2013.01); *C08G 14/08* (2013.01); *C14C 3/20* (2013.01)
  USPC ........ 424/449; 424/456; 424/78.37; 424/497; 424/78.36; 528/332; 528/172; 8/94.33

(58) Field of Classification Search
  CPC ... A61K 31/765; A61K 31/795; C08G 12/12; C08G 12/32; C08G 14/60; C08G 14/80; C14C 3/20
  See application file for complete search history.

(56) References Cited

U.S. PATENT DOCUMENTS

| 4,362,712 A | 12/1982 | Buck |
| 4,364,927 A | 12/1982 | Sipos et al. |
| 4,604,404 A | 8/1986 | Munson, Jr. et al. |
| 5,088,400 A | 2/1992 | Ferguson |
| 5,830,315 A | 11/1998 | Mitchell et al. |
| 5,843,337 A | 12/1998 | Mitchell et al. |
| 5,977,287 A | 11/1999 | Mitchell et al. |
| 6,114,476 A | 9/2000 | Krishnamurti et al. |
| 6,300,427 B1 | 10/2001 | Krishnamurti et al. |
| 2005/0138738 A1* | 6/2005 | Saravanabhavan et al. ...... 8/196 |

FOREIGN PATENT DOCUMENTS

| BE | 506674 | 11/1951 |
| CH | 139645 | 4/1930 |
| CH | 306965 | 5/1955 |
| DE | 848 823 | 7/1952 |
| DE | 1 113 457 | 9/1961 |
| DE | 33 41 122 | 5/1985 |
| DE | 10 2004 034 613 | 2/2006 |
| DE | 10 2005 050 193 | 4/2007 |
| EP | 0 037 250 | 10/1981 |
| EP | 0 301 406 | 2/1989 |
| GB | 362 797 | 12/1931 |
| JP | 2003 160626 | 6/2003 |
| SU | 487917 | 1/1976 |
| WO | 91 07183 | 5/1991 |
| WO | 95 14479 | 6/1995 |
| WO | 97 02216 | 1/1997 |
| WO | 00 09570 | 2/2000 |
| WO | 2007 131813 | 11/2007 |

OTHER PUBLICATIONS

Falbe, J. et al., "Gerbstoffe", Roempp Chemie Lexikon, Auflage, 9th Edition, pp. 1541-1542 (1995).
Okuda, T. "Systematic And Health Effects Of Chemically Distinct Tannins In Medicinal Plants", Phytochemistry, vol. 66, pp. 2012-2031 (2005).
Fukuchi, K. et al., "Inhibition Of Herpes Simplex Virus Infection By Tannins And Related Compounds", Antiviral Research, vol. 11, pp. 285-297 (1989).

* cited by examiner

Primary Examiner — David J Blanchard
Assistant Examiner — Sarah Chickos
(74) Attorney, Agent, or Firm — Oblon, Spivak, McClelland, Maier & Neustadt, L.L.P.

(57) ABSTRACT

The invention relates to a condensation product obtainable by reaction of a1) at least one bicyclic or polycyclic aromatic or heteroaromatic, where the bicyclic or polycyclic aromatic or heteroaromatic is substituted by at least one carboxyl group (—COOH), and where the carboxyl group can be present in salt form,
a2) at least one carbonyl compound,
a3) if appropriate at least one sulfonating agent,
a4) at least one urea derivative, and
a5) if appropriate at least one further aromatic or heteroaromatic, or a physiologically tolerable salt thereof.

13 Claims, No Drawings

CONDENSATION PRODUCTS BASED ON BICYCLIC OR POLYCYCLIC AROMATICS OR HETEROAROMATICS

The invention relates to a condensation product (synthetic tanning agent), as defined below, which can, if appropriate, be present as a mixture with at least one further tanning agent, and to processes for the preparation of a condensation product of this type, its use as a medicament and pharmaceutical compositions comprising a condensation product of this type. A further subject of the present invention is the use of the condensation product as a disinfectant, for example in animal stables, and a disinfectant comprising a condensation product of this type. A further subject of the present invention is the use of the condensation product as a tanning agent.

Tanning agents can in principle be divided into three main classes (see Römpps Chemie Lexikon [Römpp's chemical encyclopedia], 9th edition (1995), Georg Thieme Verlag Stuttgart, keyword "Gerbstoffe" [tanning agents], pages 1541 to 1542):
1. inorganic tanning agents such as chromium(III) salts or polyphosphates; 2. synthetic organic tanning agents which are usually obtainable by sulfonation of solubilized aldehyde condensation products of aromatic parent substances, in particular of phenol, cresol, naphthalene and naphthol; and 3. tanning agents of plant origin, as can occur in leaves (tea), seeds (coffee), berries, galls or woods. In the narrower sense, tanning agents of plant origin are understood as meaning the "tannic acids" or "tannins".

Both the tanning agents of plant origin (subsequently designated as plant or natural tanning agent) and the synthetic organic tanning agents (subsequently designated as synthetic tanning agent) are in some cases connected with antiviral action in the literature. This relates in particular to plant or synthetic tanning agents, which are designated as "polyphenols".

For example, an antiviral activity (in particular against herpes simplex) and an antitumor activity of these natural tanning agents is described for plant tanning agents such as tannins in T. Okuda, Phytochemistry, volume 66 (2005), pages 2012 to 2031 or Fukuji et al., Antiviral Res. 11 (1989), pages 285 to 298.

Furthermore, propolis, which is collected by bees from the buds, barks and resins of certain trees and comprises plant tanning agents, is ascribed, inter alia, an antiviral activity, for example against herpes simplex. Propolis, which is a complex mixture and contains, inter alia, polyphenol, can be composed, depending on the bee colony, of up to 200 different constituents, in particular these are chalkones, flavanones, flavones and flavanols (S. Bogdanov, Schweizerisches Zentrum für Bienenforschung [Swiss Center for Bee Research]; article obtainable on the Internet; http://worldwideweb.apis.admin.ch/de/bienenprodukte/docs/produkte/propolis_d.pdf).

In the case of synthetic tanning agents too, pharmaceutical applications are already known. Thus WO 95/14479 relates to a condensation polymer of aromatic sulfonic acids and an aldehyde for the inhibition of the HIV virus. It is written there that the higher the molecular weight of the polymer, the greater its therapeutic activity. Particularly preferably, condensation polymers having an $M_w$ weight of between 4000 and 12 000 g/mol are obtained by molecular size-dependent separation processes. WO 95/14479 does not, however, disclose any synthetic tanning agents which are based on aromatics or heteroaromatics having at least one carboxyl group as substituent. Furthermore, these tanning agents do not comprise any urea derivative. An analogous situation applies for U.S. Pat. No. 4,604,404, in which the use of, for example, sulfonated naphthalene-formaldehyde condensation polymers for the control of the herpes simplex virus is described. Similar compounds and, respectively, their use as medicaments are described in U.S. Pat. Nos. 5,088,400 and 4,364,927.

Furthermore, DE-A 33 41 122 describes virucidal medicaments to be used externally, in particular against herpes labilis and viral diseases of the skin. These medicaments are synthetic tanning agents, prepared by condensation of, for example, urea with phenol/cresol, formaldehyde and a sulfonating agent.

In DE-A 10 2004 034613, condensation products are described which are obtainable by reaction of at least one aromatic, at least one sulfonating agent, at least one carbonyl compound and if appropriate at least one urea derivative. Following the synthesis, the condensation products are subjected to at least one molecular size-dependent separation process. In the course of this, the condensation product was separated into three fractions, a high molecular weight, a medium molecular weight and a low molecular weight fraction. It was found that the high molecular weight fractions have an improved activity with respect to the inhibition of the activity of the enzyme human leucocyte elastase in comparison to the corresponding medium molecular weight fractions of these condensation products. DE-A 2004 034613, however, does not disclose that it is mandatory for bicyclic aromatics such as naphthalene to be substituted with a carboxyl group.

International application PCT/EP2007/051884 discloses condensation products which are analogous to DE-A 10 2004 034613 and which are prepared by reaction of at least one aromatic or heteroaromatic, with at least one carbonyl compound, if appropriate at least one sulfonating agent and if appropriate at least one urea derivative. These condensation products have an $M_w$ value ≥9000 g/mol (high molecular weight fraction) and are present as a mixture with at least one further tanning agent having an $M_w$ value ≤3000 g/mol (low molecular weight fraction). The low molecular fraction may comprise any desired tanning agent, for example a condensation product obtainable by reaction of melamine and/or urea, glyoxal, glyoxylic acid or an alkaline salt thereof and also if appropriate further components such as an aromatic compound. The low molecular weight fraction employed in these mixtures may also a be a condensation product which is coincident with the high molecular weight fraction with regard to the starting materials, but has an $M_w$ value ≤3000 g/mol. A further international application (PCT/EP 2007/051887) discloses condensation products obtainable by reaction of at least one aromatic or heteroaromatic substituted with at least one carboxyl group and with at least one hydroxyl group, at least one carbonyl compound, if appropriate at least one sulfonating agent, if appropriate at least one urea derivative and if appropriate at least one further aromatic or heteroaromatic. However, there is no disclosure in either of the aforementioned international applications that, to prepare the condensation product, the aromatic or heteroaromatic used is restricted to bicyclic or polycyclic compounds comprising at least one carboxyl group. The respective condensation products are particularly useful as an antiviral agent, for example for treating inflammations of the skin, in particular for treating herpes simplex.

CH-A 306 965 describes condensation products based on gentisic acid (dihydroxybenzoic acid) and also formaldehyde and sulfuric acid. These condensation products are useful as drugs for rheumatoid polyarthritis and also for certain infectious diseases. However, these condensation products do not comprise any urea derivative as starting component. Analogous but somewhat more broadly defined condensation products for treating infectious diseases are described in BE-A 506 674. Gallic acid and hydroxynaphthalenecarboxylic acid can also be used as starting component. The condensation products described in WO 91/07183 are useful for treating cardiovascular diseases. The starting materials used are aromatics such as salicylic acid, gallic acid or naphthalene, sulfuric acid and formaldehyde. The condensation products described in WO-91/07183 likewise comprise no urea derivative as starting component.

The German application having the number 10 2005 050 193.1, GB-A 362 797 or EP-A 0 301 406 relate to synthetic tanning agents, in particular low molecular weight tanning agents, for which no use as medicaments is described. EP-A 0 301 406 relates to condensation products obtainable by reaction of melamine with glyoxal or glyoxylic acid. Optionally, an aromatic compound is additionally condensed, selected from phenolsulfonic acid, sulfosalicylic acid, salicylic acid, or 8-hydroxychinoline. GB-A 362 797 describes condensation products prepared by reacting gallic acid or salicylic acid with cresol, sulfuric acid, urea and formaldehyde. However, it is not disclosed in any of the abovementioned documents which relate to synthetic tanning agents (condensation products) as such based on aromatics or their use as medicaments that the aromatic component employed in the respective condensation product can be bicyclic or polycyclic aromatics or heteroaromatics which have to be substituted by at least one carboxyl group or the salts thereof.

The invention is thus based on the object of making available further medicaments which are suitable as antiviral agents; preferably, these novel medicaments should have an improved action against viruses such as, for example, the herpes simplex virus. According to the invention, this object is achieved by a condensation product obtainable by reaction of a1) at least one bicyclic or polycyclic aromatic or heteroaromatic, where the bicyclic or polycyclic aromatic or heteroaromatic is substituted by at least one carboxyl group (—COOH), and where the carboxyl group can be present in salt form, a2) at least one carbonyl compound, a3) if appropriate at least one sulfonating agent, a4) at least one urea derivative, and a5) if appropriate at least one further aromatic or heteroaromatic, or a physiologically tolerable salt thereof.

An advantage of the present invention can be seen in that the condensation products according to the invention have a markedly improved activity as antiviral agents, for example against the herpes simplex virus and further viruses. The improved activity is in particular achieved by virtue of the fact that a condensation product is prepared from at least one bicyclic or polycyclic aromatic or heteroaromatic, which is substituted by at least one carboxyl group (component a1), where the carboxyl group can also be partially or completely present in salt form. In particular, a markedly improved activity arises on the use of naphthalenecarboxylic acid or salts of naphthalenecarboxylic acid. When, in the preparation of the condensation products according to the invention, the component a1) is also combined with at least one component a5), the activity can be further increased. The improved activity of the condensation products according to the invention is present both compared to conventional synthetic tanning agents based on phenol or naphthalene and compared to plant tanning agents based, for example, on gallic acid, as are comprised in green tea.

A further advantage of the present invention is that the condensation products according to the invention are also suitable for inhibiting serine proteases, in particular for inhibiting human leucocyte elastase (HALE).

When the condensation products according to the invention are used in the form of mixtures with further tanning agents, a further advantage of these mixtures according to the invention is to be seen in that in the case in which a condensation product according to the invention based on formaldehyde is employed as a mixture with a further synthetic, formaldehyde-free tanning agent, in particular using at least one condensation product (C) or (D), the proportion of formaldehyde-containing components in the mixture according to the invention can be decreased. Depending on the content of condensation product according to the invention, the activity of these mixtures is at least equal to, but usually better than in the case of synthetic tanning agents according to the prior art. This is to be seen against the background that formaldehyde, which is a widespread starting material in the preparation of synthetic tanning agents, has meanwhile been classified as a suspect carcinogen by the World Health Organisation (WHO). Accordingly, formaldehyde should be avoided in the synthesis if possible, since a certain residual formaldehyde content is always released in the case of the condensation products obtained. Since, however, an apple, for example, also comprises formaldehyde in low concentrations, accordingly low formaldehyde concentrations are tolerable in pharmaceutical compositions. The formaldehyde content is reduced, however, by means of these embodiments of the condensation products according to the invention.

The condensation product according to the invention is described more closely below.

The condensation product is obtainable by reaction of the following components a1). a2) and a4) and if appropriate a3) and a5).

a1) at least one bicyclic or polycyclic aromatic or heteroaromatic, where the bicyclic or polycyclic aromatic or heteroaromatic is substituted by at least one carboxyl group (—COOH), and where the carboxyl group can be present in salt form The terms aromatic and heteroaromatic are first defined below without taking into account the substituents (groups) carboxyl (—COON) in each case obligatorily present in each aromatic or heteroaromatic or the corresponding salt forms of this substituent. Both the aromatics and the heteroaromatics are bicyclic or polycyclic compounds.

(Bicyclic or polycyclic) aromatic is to be understood as meaning compounds i) having two condensed phenyl rings (bicycles) which can be substituted in each case independently of one another, or ii) having three and more (four, five, six, etc.) condensed phenyl systems (polycycles), where the individual cycles can be substituted in each case independently of one another. Examples thereof are naphthyl systems (bicycles), phenanthrene systems and anthracene systems (polycycles). If appropriate, in the polycyclic systems individual cycles can also be completely or partially saturated provided that at least two cycles condensed with one another are aromatic. Preferred examples of aromatics are naphthalene and anthracene, in particular naphthalene.

Systems designated as (bicyclic or polycyclic) heteroaromatic in the present invention are aromatic systems which are preferably bicyclic, if appropriate also polycyclic, and which comprise at least one heteroatom, preferably selected from nitrogen, oxygen and sulfur. Examples of a heteroaromatic are: indazole, indole, benzothiophene, benzofuran, benzothiazole, benzimidazole, quinoline, isoquinoline, quinazoline, cinnoline, quinoxaline, phthalazine, thienothiophene, 1,8-naphthyridine, other naphthyridines, purine, pteridine, acridine, phenazine, phenothiazine, phenoxazine or dibenzo-p-dioxine.

If appropriate, in the polycyclic systems individual cycles can also be completely or partially saturated provided that at least two cycles condensed with one another are aromatic. Provided they are not bicyclic systems, in the case of any of the abovementioned heteroaromatics the saturated form (perhydro form) or the partially unsaturated form (for example the dihydro form or tetrahydro form) or the maximally unsaturated (nonaromatic) form is additionally also comprised for the third (and each further) ring, provided the respective forms are known and stable. In the present invention, the term heteroaromatic thus comprises, for example, also polycycles, in which (in the case of the tricycle) all three rings are aromatic and tricycles in which only two rings are aromatic.

Apart from the obligatorily present substituents (at least once) carboxyl, the aromatics or heteroaromatics comprised in component a1) can, if appropriate, have at least one further substituent. Provided one or more further substituents are present, these are chosen independently of one another from:

$C_1$-$C_{10}$-alkyl groups such as, for example, such as methyl, ethyl, n-propyl, isopropyl, n-butyl, iso-butyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl; particularly preferably $C_1$-$C_4$-alkyl such as methyl, ethyl, n-propyl, iso-propyl, n-butyl, isobutyl, sec-butyl and tert-butyl, $C_2$-$C_{10}$-alkenyl groups, in particular vinyl, 1-allyl, 3-allyl, 2-allyl, cis- or trans-2-butenyl, ω-butenyl, $C_6$-$C_{14}$-aryl groups, such as, for example, phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl, or benzyl groups.

In one embodiment of the present invention, the bicyclic or polycyclic aromatic or heteroaromatic is not substituted with a hydroxyl group (—OH) or a hydroxyl group in salt form. Component a1) thus only comprises one or more carboxylic groups, but no hydroxyl group as substituents; if appropriate, however, further substituents can be present.

Preferably, component a1) comprises a bicyclic aromatic, preferably naphthalene. Component a1) is thus in particular at least one naphthalene, which is substituted by at least one carboxyl group, where the carboxyl group can be present in salt form.

Preferably, component a1) is a naphthalenecarboxylic acid (naphthoic acid), where the individual components can also be employed partially or completely in the form of salts, preferably as physiologically tolerable salts. Preferred naphthalenecarboxylic acids are 1-naphthalenecarboxylic acid (α-naphthalenecarboxylic acid) or 2-naphthalene-carboxylic acid (β-naphthalenecarboxylic acid; it is, however, also possible to employ naphthalenecarboxylic acid (derivatives) having two or more carboxyl groups and, if appropriate, further substituents. When further substituents are present, this is preferably not a hydroxyl group. Preferred physiologically tolerable salts of component a1) are alkali metal salts (in particular the sodium salt or the potassium salt), and alkaline earth metal salts (e.g. magnesium salt). Further preferred salts are bismuth salt. Component a1) is particularly preferably napthalenecarboxylic acid. 1-Napthalenecarboxylic acid can if appropriate be employed in the form of its salts.

a2) at least one carbonyl compound

The carbonyl compound is selected from aldehydes and ketones, preferably using at least one aldehyde such as formaldehyde, acetaldehyde, or propionaldehyde and in particular using formaldehyde. If it is desired to employ formaldehyde, it is preferred to employ formaldehyde in aqueous solution.

a3) optionally at least one sulfonating agent

Suitable sulfonating agents are, for example, sulfuric acid, in particular concentrated sulfuric acid, furthermore oleum having a content of $SO_3$ of 1 to 30% by weight, furthermore chlorosulfonic acid and amidosulfonic acid. Concentrated sulfuric acid and oleum having an $SO_3$ content of 1 to 15% by weight are preferred.

a4) at least one urea derivative

In principle, a suitable component a4) is urea and all derivatives thereof. A urea derivative is preferred which carries at least one hydrogen atom on each nitrogen atom.

Particularly preferably, at least one urea derivative is chosen from the compounds of the general formula (I)

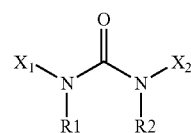

(I)

in which the variables are defined as follows:

$X^1$, $X^2$ are different or preferably identical and are chosen from hydrogen and —$CH_2OH$, $R^1$, $R^2$ are different or preferably identical and are chosen from hydrogen, $C_1$-$C_{10}$-alkyl such as, for example, methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl; particularly preferably $C_1$-$C_4$-alkyl such as methyl, ethyl, n-propyl, isopropyl, n-butyl, iso-butyl, sec-butyl and tert-butyl, or $R^1$ and $R^2$ together form a $C_2$-$C_{10}$-alkylene unit, unsubstituted or substituted by 2 to 5 hydroxyl groups, such as, for example, —$(CH_2)_2$—, —$CH_2$—$CH(CH_3)$—, —$(CH_2)_3$—, —$CH_2$—$CH(C_2H_5)$—, —$(CH_2)_4$—, —$(CH_2)_5$—, —$(CH_2)_6$—, —$(CH_2)_7$—, —$(CH_2)_8$—, —$(CH_2)_9$—, —$(CH$—$OH)_2$— (cis or trans), preferably $C_2$-$C_4$-alkylene; in particular —$(CH_2)_2$—, —$(CH_2)_3$—, and —$(CH$—$OH)_2$— (cis or trans).

Very particularly preferred urea derivatives are (unsubstituted) urea, melamine or the cyclic urea derivatives of the formulae I.1, I.2 or I.3

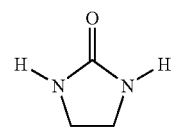

I.1

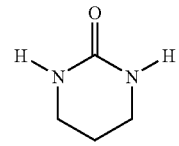

I.2

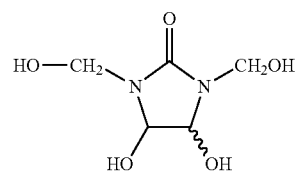

a5) if appropriate at least one further aromatic or heteroaromatic

Component a5) comprises all aromatics and heteroaromatics which do not come under the definition of component a1). Component a5) thus comprises all aromatics and heteroaromatics which are not substituted by at least one carboxyl group (—COON) (or the salt forms of these compounds) and monocyclic aromatics and heteroaromatics. The definitions of the terms "aromatic" and "heteroaromatic" correspond to that of component a1) and additionally comprise any monocyclic systems and bi- or polycyclic systems which have only one aromatic cycle, while the further cycles are completely or partially hydrogenated. Component a5) accordingly also comprises unsubstituted aromatics such as benzene, compounds having at least one hydroxyl group, but no carboxyl group, such as phenol or resorcinol, and compounds having at least one carboxyl group, but no hydroxyl group, such as benzoic acid or phthalic acid.

Examples of suitable monocyclic heteroaromatics according to component a5) are: pyrrole, furan, thiophene, imidazole, pyrazole, 1,2,3-triazole, 1,2,4-triazole, 1,3-oxazole (=oxazole), 1,2-oxazole (=isoxazole), oxadiazole, 1,3-thiazole (=thiazole), 1,2-thiazole (=isothiazole), tetrazole, pyridine, pyridazine, pyrimidine, pyrazine, 1,2,3-triazine, 1,2,4-triazine, 1,3,5-triazine or 1,2,4,5-tetrazine, Examples of partially hydrogenated, bicyclic heteroaromatics are: 3H-indoline, 2(1H)-quinolinone, 4-oxo-1,4-dihydroquinoline, 2H-1-oxoisoquinoline, 1,2-dihydroquinoline, 3,4-dihydroquinoline, 1,2-dihydroisoquinolinyl, 3,4-dihydroisoquinoline, oxindolyl, 1,2,3,4-tetrahydro-isoquinoline, 1,2,3,4-tetrahydroquinoline, 5,6-dihydroquinoline, 5,6-dihydroisoquinoline, 5,6,7,8-tetrahydroquinoline or 5,6,7,8-tetrahydroisoquinoline.

Preferably, component a5) is at least one aromatic or heteroaromatic selected from benzene, naphthalene, anthracene, aromatic alcohols, aromatic ethers and aromatic sulfones, where the aforementioned compounds can be optionally substituted.

Examples of preferred aromatics or heteroaromatics according to component a5) are: benzene, toluene, ortho-xylene, meta-xylene, para-xylene, ethylbenzene, cumene, para-methylcumene, biphenyl, 2-methylbiphenyl, 3-methylbiphenyl, 4-methylbiphenyl, bitolyl(4,4'-dimethylbiphenyl), para-terphenyl, indene, fluorene, methylindenes (isomer mixture). Naphthalene, 1-methylnaphthalene, 2-methylnaphthalene, 1,8-dimethyl-naphthalene, 2,7-dimethylnaphthalene, phenanthrene, anthracene, 9-methyl-anthracene, 9-phenylanthracene.

Examples of aromatic alcohols which may be mentioned are: phenol, ortho-cresol, meta-cresol, para-cresol, 2-ethylphenol, 3-ethylphenol, 4-ethylphenol, 2,3-dimethylphenol, 2,4-dimethylphenol, 2,5-dimethylphenol, 2,6-dimethylphenol, 3,4-dimethylphenol, 3,5-dimethylphenol, α-naphthol, β-naphthol, 9-hydroxyanthracene as a tautomer of anthrone, 9-hydroxyphenanthrene, diphenylmethane, phenyl-(2-methyl-phenyl)methane, phenylparatolylmethane, phenylmetatolylmethane.

Examples of aromatic ethers which may be mentioned are: diphenyl ether, di-ortho-tolyl ether, di-meta-tolyl ether and di-para-tolyl ether.

Examples of aromatic sulfones which may be mentioned are diphenyl sulfone and dihydroxydiphenyl sulfone, in particular 4,4'-dihydroxydiphenyl sulfone.

Component a5) is particularly preferably phenol.

In one preferred embodiment of the present invention, the preparation of the condensation product, as well as the components a1), a2) and a4) also utilizes at least one component a3) and/or at least one component a5) as reactant. In one more preferred embodiment, the preparation of the condensation product utilizes at least one each of components a1) to a5). Preferably, one component a1) and one component a5) is used.

In one embodiment of the present invention, mixtures of at least 2 aromatics are employed as component a5), for example mixtures of naphthalene and phenol, naphthalene and cresol (isomer mixture), naphthalene and diphenyl ether, naphthalene and ditolyl ether or phenol and ditolyl ether. Further embodiments involve mixtures of phenol and gallic acid or salicylic acid or salts thereof.

In a further embodiment of the present invention, monocyclic aromatics or heteroaromatics are employed as component a5), preferably gallic acid (trihydroxybenzoic acid), salicylic acid or their mixtures or salts thereof, in particular gallic acid.

In a further preferred embodiment, the condensation product according to the invention is obtainable by reaction of a1) 1-napthalenecarboxylic acid or a salt thereof,
a2) at least one aldehyde selected from formaldehyde, acetaldehyde and propionaldehyde
a3) concentrated sulfuric acid
a4) at least one urea derivative selected from urea, melamine,

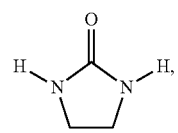

I.1

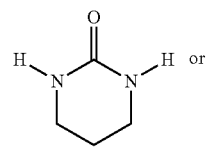

I.2

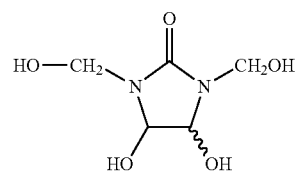

I.3 and
a5) if appropriate phenol

Processes for the preparation of a condensation product according to the invention are known to the person skilled in the art, for example they are described in EP-A 37 250, DE-A 1 113 457, Ullmann's Encyclopedia of Industrial Chemistry, volume A15, (5th edition) Weinheim 1990, pp. 259-282 or DE-A 848 823.

The individual components a1), a2) and a4) and if appropriate a3) and a5) can be reacted here in one or in a number of stages. For example, it is possible first a1) to react at least one bicyclic or polycyclic aromatic or heteroaromatic substituted by —COON
a3) if appropriate with at least one sulfonating agent and then to react the product in the same vessel, without prior isolation, with
a2) at least one carbonyl compound,
a4) at least one urea derivative and
a5) if appropriate at least one further aromatic or heteroaromatic.

Alternatively, the sequence of the addition of the components a1) and a5) can be exchanged or a1) and a5) are added at least once in the form of a mixture.

It is possible to proceed in another embodiment by
a1) reacting at least one bicyclic or polycyclic aromatic or heteroaromatic substituted by —COOH
a3) if appropriate with at least one sulfonating agent, isolating the product and then reacting it with the reaction product of
a2) at least one carbonyl compound,
a4) at least one urea derivative and
a5) at least one further aromatic or heteroaromatic.

In one embodiment of the present invention it is possible to bring components a1), a2) and a4) and if appropriate a3) and a5) to reaction in one portion in each case.

In another embodiment of the present invention at least one component a1) to a5) is brought to reaction in at least two portions. Preferably, these are components a1), a2) and/or a5), in particular component a2). This means that the second portion—in maximally equimolar amounts to the first portion—is added to the reaction vessel after reaction of the other components and a "recondensation" is carried out.

In a specific embodiment of the present invention a number of components a1), a2) and a4) and if appropriate a3) and a5) are brought to reaction in a number of portions.

In one embodiment of the present invention, it is possible during the reaction
a6) to add one or more further components, for example $NaHSO_3$, $Na_2S_2O_5$, $KHSO_3$, $K_2S_2O_5$, aqueous alkali metal hydroxide solution, in particular aqueous sodium hydroxide solution and aqueous potassium hydroxide solution, and aqueous ammonia. Furthermore, complexing agents are also suitable as component a6), for example complexing agents based on ethylenediaminetetraacetic acid. An example of such a complexing agent is the commercial product Trilon B (BASF AG, Ludwigshafen, Germany), which comprises ethylenediaminetetraacetate (EDTA). These complexes are stable to temperature variations (preferably up to at least 100° C.) and pH variations. The complexing agents promote the formation of water-soluble complexes with ions. Component a6) is used in particular for the adjustment of the pH and the control of the solubility of the end product.

If component a6) is comprised in the condensation products according to the invention, the ratio a1) to a6) is 10 to 99% by weight to 1 to 90% by weight, in particular 30 to 80% by weight to 20 to 70% by weight.

In one embodiment of the present invention, the components a1) to a6) are chosen in the following ratio:
a1) in the range from altogether 10 to 70% by weight (percent by weight), preferably altogether 20 to 60% by weight, particularly preferably altogether 35 to 50% by weight,
a2) in the range from altogether 5 to 40% by weight, preferably altogether 10 to 30% by weight, particularly preferably altogether 15 to 25% by weight,
a3) if appropriate in the range from altogether 5 to 50% by weight, preferably altogether 10 to 40% by weight, particularly preferably altogether 20 to 30% by weight, sulfonating agents always being calculated as $SO_3$,
a4) if appropriate in the range from 0 to altogether 30% by weight, preferably altogether 10 to 25 and particularly preferably 15 to 25, % by weight,
a5) if appropriate in the range from altogether 10 to 70% by weight, preferably altogether 20 to 60% by weight, particularly preferably altogether 35 to 50% by weight,
where % by weight is in each case based on the sum of all components a1) to a4), and if appropriate a5),
a6) in the range from 0 to altogether 30% by weight, preferably to altogether 25% by weight and particularly preferably altogether to 20% by weight,
where the % by weight details of a6) are based on the sum of the components a1), a2) and a4), if appropriate a1) to a5).

It is possible to react, for example, at temperatures in the range from 40 to 200° C., preferably 50 to 110° C. Customarily, the temperature of the reaction here is adapted to a1) and a2). If it is desired, for example, to react aromatic alcohols, it is preferred to react at temperatures in the range from 50 to 110° C. Of course, it is also possible to adjust a certain temperature profile during the reaction. Thus it is possible, for example, to start the reaction first at 90 to 100° C. and after some time, for example after 2 to 10 hours, to cool it to 40 to 75° C. and to complete the reaction over a period of time of, for example, 1 to 10 hours.

Reaction is carried out, for example, at atmospheric pressure, but can also be carried out, if desired, at higher pressures, for example 1.1 to 10 bar.

By means of the reaction described above, reaction solutions are obtained which customarily comprise large amounts of acids such as, in particular, sulfuric acid or—in the case of the use of chlorosulfonic acid—HCl. Furthermore, reaction solutions can comprise large amounts of alkali metal sulfate and/or alkali metal chloride.

Following the reaction described above, a pH in the range from 3 to 10, preferably 3.5 to 9, can be adjusted using, for example, aqueous alkali metal hydroxide solution or aqueous ammonia.

By addition of water to the reaction solutions obtainable by means of the reaction described above, it is possible by dilution with water to set a water content in the range from 70 to 95% by weight, preferably 75 to 90% by weight.

On account of the carboxyl group obligatorily present in component a1) and further acidic or basic groups possibly present in the individual components, the present invention also comprises the corresponding physiologically or toxicologically tolerable salts of the condensation products according to the invention. If appropriate, the condensation products according to the invention can be converted to physiologically tolerable salts following their preparation.

On account of their higher water solubility, physiologically tolerable salts are particularly suitable for medicinal applications compared to the starting or base compounds. These salts must have a physiologically tolerable anion or cation. Suitable physiologically tolerable acid addition salts of the compounds according to the invention are salts of inorganic acids, such as hydrochloric acid, hydrobromic acid, phosphoric acid, metaphosphoric acid, nitric acid, sulfonic acid and sulfuric acid, and organic acids, such as, for example, acetic acid theophyllineacetic acid, methylene-bis-b-oxynaphthoic, benzene-sulfonic, benzoic, citric, ethanesulfonic, salicylic, fumaric, gluconic, glycolic, isethionic, lactic, lactobionic, maleic, malic, methanesulfonic, succinic, p-toluenesulfonic, tartaric and trifluoroacetic acid. Suitable pharmaceutically tolerable basic salts are ammonium salts, alkali metal salts (such as sodium and potassium salts) and alkaline earth metal salts (such as magnesium and calcium salts).

Salts having a not pharmaceutically tolerable anion are also included in the context of the scope of the invention as useful intermediate products for the preparation or purification of pharmaceutically tolerable salts and/or for use in non-therapeutic, for example in-vitro, applications.

The corresponding salts of the condensation products according to the invention can be obtained by conventional methods which are known to the person skilled in the art, for example by reaction with an organic or inorganic acid or base in a solvent or dispersant, or by anion or cation exchange with other salts.

The present invention moreover additionally includes all solvates of the condensation products, for example hydrates or adducts with alcohol, active metabolites and derivatives which comprise a physiologically acceptable and cleavable group, for example esters or amides.

The term "physiologically functional derivative" herein designates any physiologically tolerable derivative of a condensation product according to the invention, e.g. an ester, which on administration to a mammal, such as, for example, a human, is able, (directly or indirectly) to form a condensation product according to the invention or an active metabolite thereof. Examples of these are acetylphenoxy derivatives, obtainable by reaction of acetic anhydride and one of the phenol groups present.

The physiologically functional derivatives also include prodrugs of the condensation products according to the invention. Such prodrugs can be metabolized in vivo to give a condensation product according to the invention. These prodrugs can be active or not active themselves and are likewise a subject of the present invention.

The condensation products according to the invention can also be present in various polymorphic forms, e.g. as amorphous and crystalline polymorphic forms. All polymorphic forms of the condensation products according to the invention are included in the scope of the invention and are a further aspect of the invention.

In a further embodiment of the present invention, in the preparation of the condensation product according to the invention, after reaction of components a1), a2) and a4) and if appropriate a3) and a5) a molecular size-dependent separation process can be carried out, preferably an ultrafiltration with retention of individual fractions of the condensation product according to the invention, for example a low molecular weight, a medium molecular weight and a high molecular weight fraction. Analogously, this also applies for the condensation products (B) described below. The high molecular weight fraction, for example, has an $M_w$ value $\geq 9000$ g/mol ($M_w$=weight average molecular weight), preferably an $M_w$ value of 10 000 to 100 000 g/mol. The low molecular weight fraction preferably has an $M_w$ value of 300 to 3000 g/mol. Preferably, in the high molecular weight fraction of the ratio $M_w/M_n$ is <10, in particular $M_w/M_n$ is <5 ($M_n$=number average molecular weight).

With respect to molecular size-dependent separation processes, the following, for example, are suitable: preparative gel permeation chromatography and membrane separation processes such as, for example, microfiltration, nanofiltration and in particular ultrafiltration. Combinations of a microfiltration and ultrafiltration are also suitable. Microfiltrations and ultrafiltrations and membranes necessary therefor are known as such and are described, for example, in Ullmann's Encyclopedia of Industrial Chemistry, 6th edition, vol. 21, Wiley-VCH Weinheim, pp. 243-321. Nanofiltrations and the relevant membranes therefor are likewise known as such and are described in R. Rautenbach, "Membranverfahren" [Membrane Processes]", Springer Verlag Berlin Heidelberg 1997.

Ultrafiltrations are known as such and are in general operated as crossflow ultrafiltrations. Suitable membranes are commercially available membranes which are prepared, for example, from organic materials such as polysulfones or polyvinylidene fluoride or preferably from inorganic materials such as, for example, $TiO_2$, $ZrO_2$ or $Al_2O_3$. Customary forms are capillary, tubular and flat membranes, the latter in the form of membrane pads or spirally wound modules.

For example, during membrane separation processes and in particular during ultrafiltrations a transmembrane pressure difference, i.e. a pressure difference between feed and permeate, in the range from 1 to 200 bar, preferably in the range from 1.2 to 100 bar, is used.

In one embodiment, the temperature of the reaction solution treated after membrane separation processes is in the range from 20 to 70° C., preferably 25 to 35° C.

In one embodiment of the present invention, at least one membrane having a molecular weight cut-off in the range from 1000 daltons, preferably 2000 daltons, particularly preferably 5000 daltons, very particularly preferably 7500 daltons and even more preferably of 15 000 daltons, is set. The molecular weight cut-off is also designated as the separation limit.

In one embodiment of the present invention, the ultrafiltration is carried out such that a certain mass ratio of permeate to retentate is set at the end of the ultrafiltration. The amount of retentate customarily remains constant in the ultrafiltration due to continuous readdition of water, the amount of permeate increases in the course of the filtration time. Customary values are in the range from 0.5:1 to 10:1, preferably 0.8:1 to 5:1, particularly preferably 1.0:1 to 3:1.

Customarily, visually essentially transparent aqueous solutions of condensation products are obtained.

It is possible to isolate the condensation products from the solutions described above, for example by evaporation of the water or by spray drying.

In one embodiment of the present invention, the condensation products have a salt content of inorganic salts such as, for example, alkali metal sulfate and alkali metal chloride of 10 ppm to less than 5% by weight, preferably less than 2% by weight, particularly preferably less than 1% by weight and very particularly preferably less than 0.5% by weight, based on the dry weight of condensation product. The salt content can be determined, for example, by ion chromatography (IC), as described, for example, in Römpps Lexikon Chemie, 10th edition, Georg Thieme Verlag Stuttgart• New York, volume 2, keyword: lonenchromatographie (ion chromatography).

In one embodiment of the present invention, the condensation products have a residual monomer content of 10 ppm to less than 5% by weight, preferably less than 2% by weight, based on the dry weight of the condensation product. Residual monomers are designated in the context of the present invention as unreacted reactants a1), a2), a4) and if appropriate a5) which can be found in the condensation products. The residual monomer content can be determined, for example, by gel permeation chromatography (GPC) or preferably by ion chromatography (IC) or high pressure liquid chromatography (HPLC).

In one embodiment of the present invention, condensation products according to the invention have a content of free carbonyl compound a2), including carbonyl compound a2) present as a hydrate, in the range from 1 ppm to less than 0.5% by weight, preferably 0.1% by weight or less, based on the dry weight of condensation product according to the invention. In this embodiment, the amount of free carbonyl compound a2) relates of course to the carbonyl compound a2) which has been employed in the reaction of a1), a2) and a4) and if appropriate a3) and a5). If a number of carbonyl compounds a2) have been employed, the content of free carbonyl compound a2) relates to the sum of all carbonyl compounds a2) which has been employed in the reaction of a1), a2) and a4) and if appropriate a3) and a5). The determination of the content of free carbonyl compound a2) can be carried out according to methods known per se. If carbonyl compound a2) is solid or liquid at room temperature, the content of free carbonyl compound a2) can be determined, for example, by gas chromatography or HPLC. If carbonyl compound a2) is formaldehyde, it can be determined, for example, photometrically. A particularly preferred method for the determination of free formaldehyde is the reaction with acetylacetone and ammonium acetate to give diacetyldihydrolutidine and photometric measurement of diacetyldihydrolutidine at a wavelength of 412 nm.

In one embodiment of the present invention, the condensation product described above is employed as a mixture with at least one (further) tanning agent, in particular a synthetic or plant tanning agent. In one embodiment, the $M_w$ value of the further tanning agent is ≤3000 g/mol; an $M_w$ value of between 300 and 3000 g/mol is preferred.

The further tanning agent can be either an inorganic tanning agent, a plant tanning agent or a synthetic tanning agent (for this see the aforementioned definition according to Römpp's Chemie Lexikon, 9th edition (1995), Georg Thieme Verlag, Stuttgart, keyword: "Gerbstoffe" [tanning agents], pages 1541 to 1542). Preferably, the further tanning agents used are plant or synthetic tanning agents; synthetic tanning agents are particularly preferred here. In one embodiment, those tanning agents which comprise no formaldehyde as a starting material are preferred.

The further tanning agent can be added to the condensation product according to the invention in any desired concentration. Preferably, the condensation product according to the invention is present in a mixture of this type to at least 50% by weight based on the sum of the tanning agents.

Examples of plant tanning agents are tannins such as catechols or gallic acid derivatives such as gallates. Plant tanning agents which are based on gallic acid derivatives (such as gallates) differ from the condensation products according to the invention in particular in that the last-mentioned have in their chemical structures (a multiplicity of) —$CR^1R^2$ bridges (crosslinkages), which are derived from the carbonyl compound a2) employed and which are not present in plant tanning agents. If, for example, formaldehyde is employed as component a2), the condensation products have —$CH_2$ bridges. Plant tanning agents (gallates) are typically oligomeric systems, whereas the condensation products according to the present invention are preferably polymers. In one embodiment, the condensation products have a molecular weight $M_w$ ≥800 g/mol, preferably ≥2500 g/mol, in particular 10 000 to 50 000 g/mol.

Preferred plant tanning agents are tannins from the group consisting of the catechols, epicatechols and epigallocatechols and their gallates.

Tannin is understood in principle as meaning naturally occurring polyphenols, such as are mentioned, for example, in T. Okuda Phytochemistry, volume 66 (2005), pages 2012 to 2031 or Römpp's chemical encyclopedia, 9th edition (1995), Georg Thieme Verlag, Stuttgart, keyword "Tannine" [tannins], pages 4452 to 4453. Preferred tannins are ellagitannins and dehydroellagitannins, in particular geraniin, dehydrogeraniin, furosinin, ascorgeraniin, geraniinic acid, mallotusinic acid, pentagalloylglucose, camelliatannin A, casuariin, euphorbin E, camelliatannin F, agrimoniin, trapanin B, oenothein A, oenothein B or gemin D, lignin and lignosulfonates. Catechols, epicatechols and epigallocatechols are furthermore preferred.

Examples of a suitable catechol or derivatives thereof comprise, in particular, flavan-3-ols, flavan-3,4-diols(leucoanthocyanidins) and flavanones, flavones, chalcones or dihydrocychalcones, epicatechols and epigallocatechols.

Examples of suitable plant gallic acid derivatives are mentioned, for example, in H. Sakagami et al, Anticancer Research 17 (1997), pages 377 to 380. Preferably, these are methyl tri-O-methylgallate, tri-O-methylgallic acid, methyl tri-O-acetylgallate, methyl gallate, ethyl gallate, n-propyl gallate, isoamyl gallate, lauryl gallate, stearyl gallate, epigallocatechol gallate and gallic acid.

For example, extracts of green tea can also be employed as plant tanning agents, just as extracts of chestnuts or mimosa.

Synthetic tanning agents as such and processes for their preparation are known to the person skilled in the art. Suitable synthetic tanning agents, preferably having an $M_w$ value ≤3000 g/mol, are disclosed, for example, in EP-A 0 301 406 or DE-A 10 2005 050 193.1. Methods how, by control of the synthesis parameters, the molar mass can be controlled within a certain range, are known to the person skilled in the art.

Preferably, the mixtures according to the invention comprise as a synthetic tanning agent at least one of the condensation products (B) to (D) listed below.

Condensation Product (B)

Condensation product (B) is obtainable by reaction of
b1) at least one aromatic or heteroaromatic,
b2) at least one carbonyl compound,
b3) if appropriate at least one sulfonating agent and
b4) if appropriate at least one urea derivative.

Components b1) to b4) correspond, including the preferred definitions, to components a2) to a5) of the condensation product according to the invention, component b1) corresponding to component a5). Furthermore, unlike component a5), other than phenol, dihydroxydiphenyl sulfone, in particular 4,4'-dihydroxydiphenyl sulfone, is also a particularly preferred component b1).

In one embodiment of the present invention, the condensation products (B) have an $M_w$ value ≤3000 g/mol. Processes for the preparation of condensation products (B) having a low $M_w$ value ($M_w$ values ≤3000 g/mol) are known to the person skilled in the art. Condensation products of this type can be selectively prepared, in particular, by influencing parameters such as reaction time, temperature (rather lower), the choice of the monomers (influences the reactivity, in particular use of dihydroxydiphenyl sulfones or pH (weakly acidic). Alternatively, condensation products (B) can also be prepared by carrying out—as described for the condensation product according to the invention—following the synthesis of an appropriate condensation product, a molecular size-dependent separation process, preferably an ultrafiltration, the condensation product (B) being isolated from all other constituents. Condensation products (B) having the desired $M_w$ value can be separated off and isolated, in particular, by use of a membrane having a suitable molecular weight cut-off range of 1000 D-2500 D.

Condensation Product (C)

Condensation product (C) is obtainable by reaction of
c1) melamine and/or urea,
c2) glyoxal, glyoxylic acid or an alkali metal salt thereof,
c3) if appropriate at least one aromatic compound having at least one phenolic hydroxyl group and
c4) if appropriate at least one condensable compound having a reactive nitrogen-containing group.

The condensation products (C) as such and processes for their preparation are known to the person skilled in the art. For example, these are described in EP-A 0 301 406 and are additionally incorporated in the present invention by way of reference.

Suitable components c3) are, for example, phenolsulfonic acid, sulfosalicylic acid, salicylic acid and 8-hydroxyquinoline or 4,4'-dihydroxydiphenyl sulfone. Suitable components c4) are carboxylic acid amides, sulfonic acid amides, imides, ureas, amino and imino acids and dialkylamines and dialkanolamines. Examples of these are acetamide, benzoic acid amide, formamide, amidosulfonic acid, succinimide, glycine, iminodiacetic acid, phenylglycine, urea, dicyandiamide, diethanolamine or diethylamine. Acidic compounds can be condensed here in the form of their alkali metal salts. A particularly preferred component c4) is acetamide or amidosulfonic acid.

A preferred condensation product (C) is obtainable by reaction of
c1) melamine and/or urea,
c2) glyoxal and/or glyoxylic acid and
c4) if appropriate amidosulfonic acid.

Condensation Product (D)

Condensation product (D) is obtainable by reaction of
d1) at least one cyclic organic carbonate with
d2) at least one compound having at least two nucleophilic groups per molecule, chosen from sulfonic acid, hydroxyl, primary or secondary amino or mercapto groups.

Condensation products (D) as such and processes for their preparation are known to the person skilled in the art; they are disclosed, for example, in the German application having the number DE-A 10 2005 050 193.1 and are additionally incorporated in the present invention by way of reference.

Cyclic organic carbonates (component d1) are understood in the context of the present invention as meaning organic carbonic acid esters which have at least one cyclic group.

Preferably, cyclic organic carbonates are organic carbonic acid esters of the type in which the carbonic acid ester group is a constituent of a cyclic system.

In one embodiment of the present invention, cyclic organic carbonate (d1) is chosen from compounds of the general formula (II)

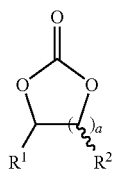

(II)

Where the variables are defined as follows:
$R^1$ is chosen from $C_1$-$C_4$-alkyl, branched or preferably linear, for example methyl, ethyl, n-propyl, isopropyl, n-butyl, isobutyl, sec-butyl, tert-butyl, very preferably methyl and ethyl, and very particularly preferably hydrogen,
$R^2$ if appropriate different or preferably identical and independently of one another chosen from hydrogen and $C_1$-$C_4$-alkyl, branched or preferably linear, for example methyl, ethyl, n-propyl, isopropyl, n-butyl, isobutyl, sec-butyl, tert-butyl, very preferably methyl and ethyl, and very particularly preferably in each case identical, and hydrogen,
a an integer in the range from 1 to 3, preferably 2 and particularly preferably 1.

Particularly preferred cyclic organic carbonates d1) are propylene carbonate or ethylene carbonate. Mixtures of propylene carbonate ($R^1$=methyl, $R^2$=hydrogen, a=1) and ethylene carbonate ($R^1$=$R^2$=hydrogen, a=1), in particular mixtures of propylene carbonate and ethylene carbonate liquid at room temperature are likewise particularly preferred.

Component d2) is understood as meaning compounds of the type which have two groups capable of nucleophilic reactions such as, for example, sulfonic acid groups, hydroxyl groups, mercapto groups or primary or secondary amino groups.

Examples of suitable compounds d2) can have:
at least two nucleophilic hydroxyl groups per molecule,
at least two nucleophilic Mercapto groups per molecule,
at least two nucleophilic primary or secondary amino groups per molecule, for example two or three nucleophilic primary or secondary amino groups per molecule,
at least one nucleophilic hydroxyl group or mercapto group and at least one nucleophilic primary or secondary amino group per molecule or
at least one nucleophilic hydroxyl group and at least one nucleophilic mercapto group per molecule,
at least one nucleophilic hydroxyl group or primary or secondary amino group and one sulfonic acid group per molecule.

Sulfuric acid is not a compound d2) within the meaning of the present invention.

Examples of nucleophilic hydroxyl groups are OH groups of primary and secondary alcohols and in particular phenolic OH groups.

Examples of nucleophilic mercapto groups are SH groups, aliphatic or aromatic.

Examples of nucleophilic amino groups are —$NHR^3$ groups, aliphatic or aromatic, where $R^3$ is chosen from hydrogen, $C_1$-$C_4$-alkyl, as defined above, and CN, or the $NH_2$ group of, for example, amidosulfonic acid.

OH groups and NH groups which are constituents of animal groups, hemiaminal groups or hydrate groups of ketones or aldehydes are not nucleophilic hydroxyl groups or amino groups within the meaning of the present invention. OH groups and NH groups which are constituents of carboxylic acid groups or carboxylic acid amido groups are also not nucleophilic hydroxyl groups or amino groups within the meaning of the present invention.

Preferred examples of compounds d2) are
i) ureas, unsubstituted or mono- or di-N,N'-substituted by $C_1$-$C_4$-alkyl, biuret, in particular unsubstituted urea,
ii) heterocyclic compounds having at least two $NH_2$ groups per molecule, for example adenine and in particular melamine,
iii) benzoguanamine, dicyandiamide, guanidine,
iv) compounds of the general formula (III)

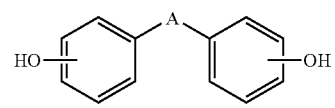

(III)

in which A is a bivalent group, for example —$CH_2$—, —$CH_2CH_2$—, —$CH(CH_3)$—, —$C(CH_3)_2$—, —CO—, —$SO_2$—, preferably 4,4'-dihydroxybiphenyl, 2,4'-dihydroxydiphenyl sulfone, particularly preferably 4,4'-dihydroxydiphenyl sulfone, mixtures of 4,4'-dihydroxydiphenyl sulfone and 2,4'-dihydroxydiphenyl sulfone, for example in a weight ratio of 8:1 to 8:1.5, and bisphenol A.

Further preferred examples of compound d2) are 4-hydroxyphenylsulfonic acid and amidosulfonic acid.

Particularly preferred compounds d2) are selected from melamine, biuret, dicyanamide, amidosulfonic acid and 4,4'dihydroxydiphenyl sulfone.

In one embodiment of the present invention, mixtures are employed in which at least one condensation product according to the invention and/or at least one synthetic tanning agent having an $M_w$ value ≤3000 g/mol are prepared using at least one compound which comprise at least one hydroxyl group or is substituted by a group of this type. Preferably, this is achieved by the component a5) comprising at least one compound which is substituted by at least one hydroxyl group and/or
the component b1) comprising at least one compound which is substituted by at least one hydroxyl group and/or
the component c3) being present and/or
the component d2) comprising at least one compound having at least one hydroxyl group as a nucleophilic group.

In a further preferred embodiment of the present invention, mixtures are employed in which the further tanning agent is formaldehyde-free, preferably a synthetic formaldehyde-free tanning agent. Preferably, this is achieved by employing a condensation product (C) or condensation product (D) in the mixture.

The present invention furthermore relates to the use of the condensation products according to the invention, if appropriate in the context of one of the mixtures described above, as a drug or medicament.

The condensation products according to the invention are suitable, in particular, as an antiviral agent, that is as drugs against viruses, also called virustatics or virucidal agents. Preferably, they are suitable as an antiviral agent against human papillomaviruses, especially type 16, 18, 6 and 11, endogenous retroviruses, in particular the HERV type (human endogenous retroviruses), herpes viruses, in particular HSV-1, HCMV viruses (human cytomegalovirus) or HIV viruses.

Furthermore, the condensation products according to the invention are preferably suitable as an antiviral agent against coronaviruses (e.g. SARS (severe acute respiratory syndrome)—associated coronavirus), flaviviruses (e.g. West Nile Virus (WNV)), togaviruses (e.g. Chikungunya virus) or paramyxoviruses (e.g. measles, respiratory syncytial virus (RSV)).

The condensation products according to the invention are further preferably useful for inhibiting serine proteases. Serine proteases comprise human leucocyte elastase (HLE; also referred to as human neutrophil elastase (HNE)), proteinase 3 and cathepsin G. Preferably, the serine proteases comprise HLE or proteinase 3, in particular HLE.

Preferably, the condensation products according to the invention are suitable (for the production of a medicament) for the prophylaxis and/or treatment of genital warts, cancer of the uterine cervix, allergic or nonallergic eczema, in particular neurodermatitis (endogenous eczema), diaper rash, pruritus, inflammatory diseases, autoimmune diseases, in particular arthritis, rheumatism, of melanomatous carcinomas, inflammations of the skin, herpes, in particular herpes labilis and herpes simplex, chickenpox, herpes zoster, influenza or Aids (HIV).

The condensation products according to the invention are further useful for prophylaxis and/or treatment of lung diseases, myocardial perfusion, ischemic brain damage, peritonitis, septic shock or systemic vasculitides. The lung diseases in question preferably comprise chronic obstructive pulmonary diseases (COPDs). Preferably, the condensation product according to the invention is administered in the form of an aerosol in the case of the lung diseases. The systemic vasculitides preferably comprise Wegener's granulomatosis.

The condensation products according to the invention are further useful for prophylaxis and/or treatment of bullous pemphigoid, psoriasis vulgaris, the allergenic potency of type 1 allergens, allergic rhinitis, allergic conjunctivitis, allergic bronchial asthma or psoriasis.

In one embodiment of the present invention, drugs are drugs for the local treatment of allergic or nonallergic eczema, diaper rash or pruritus. Preferably, neurodermatitis (endogenous eczema) is treated in this embodiment.

In one specific embodiment of the present invention, drugs are drugs for the treatment of inflammatory diseases of the skin, in which, owing to enzymatic activity, for example, of human leucocyte elastase, the formation of vesicles, pustules and "spongiosis" in the epidermis occurs. The drugs are preferably applied externally.

In a preferred embodiment of the present invention, drugs are drugs against viruses, preferably retroviruses, for example RNA viruses (ribonucleic acid viruses) and DNA viruses (deoxyribonucleic acid viruses) and in particular herpes viruses, for example viruses which produce herpes simplex (HS viruses), or even viruses which produce chickenpox and influenza. It is further to be noted that the active compounds according to the invention can be employed both against hydrophilic and, just as effectively, against lipophilic/hydrophobic viruses.

In a further embodiment of the present invention, drugs are drugs against HIV viruses (human immunodeficiency virus). The HIV virus is known for the fact that it causes Aids (acquired immunodeficiency syndrome).

In a further preferred embodiment of the present invention, drugs are drugs against human papillomaviruses and of endogenous retroviruses (HERV type). Human papillomaviruses are in particular the type 16, 18, 6 and 11. In this respect, the condensation products according to the invention are suitable, in particular, for the external medication of genital warts and cancer of the uterine cervix. In connection with the treatment of HERV viruses (in particular HERV-K), the condensation product according to the invention is suitable for the treatment of autoimmune diseases (arthritis) and preventively against melanomatous carcinoma.

In the foregoing explanations, the term treatment also comprises the prophylaxis, therapy or cure of the aforementioned diseases.

The condensation products according to the invention can be administered to animals and humans, preferably mammals and humans, particularly preferably humans. The condensation products according to the invention can here be administered themselves as drugs, in mixtures with one another or mixtures with other drugs or in the form of pharmaceutical compositions. Consequently, the use of the condensation products according to the invention for the production of one or more medicaments for the prophylaxis and/or treatment of the aforementioned diseases or as an antiviral agent, pharmaceutical compositions comprising an efficacious amount of at least one condensation product according to the invention and the use of these pharmaceutical compositions for the prophylaxis and/or treatment of the aforementioned diseases are likewise a subject of the present invention.

The pharmaceutical compositions according to the invention comprise an efficacious amount of at least one condensation product according to the invention and a physiologically tolerable vehicle. The pharmaceutical compositions can be present here in different administration forms, in particular in the form of a pill, tablet, lozenge, granules, capsule, hard or soft gelatin capsule, aqueous solution, alcoholic solution, oily solution, syrup, emulsion, suspension, suppository, pastille, solution for injection or infusion, ointment, tincture, cream, lotion, cosmetic powder, spray, of a transdermal therapeutic system, nasal spray, aerosol, aerosol mixture, microcapsule, implant, rod, patch or gel. Likewise, the pharmaceutical composition according to the invention can also be a constituent of healthcare products such as sunscreen creams, nasal sprays, mouthwashes, toothpastes, plasters, (wet) wipes, cleansing lotions or shampoos.

Depending on the administration form used, the condensation products according to the invention are processed with physiologically tolerable vehicles, which are known as such to the person skilled in the art, to give the pharmaceutical compositions according to the invention. The vehicle must of course be tolerable in the sense that it is compatible with the other constituents of the composition and is not harmful to health for the patient (physiologically tolerable). The vehicle can be a solid or a liquid or both and is preferably formulated with the compound as an individual dose, for example as a tablet, which can comprise from 0.05 to 95% by weight of the active compound (condensation product according to the invention). Further pharmaceutically active substances can likewise be present. The pharmaceutical compositions according to the invention can be produced according to one of the known pharmaceutical methods, which essentially consist in mixing the constituents with pharmacologically tolerable vehicles and/or further excipients such as fillers, binders, lubricants, wetting agents, stabilizers et cetera.

Preferred pharmaceutical compositions in the context of the present invention are mentioned below.

In one embodiment of the present invention, ointments, creams, fatty creams, gels, lotions or powders according to the invention can in each case be comprised in the range from 0.1 to 5% by weight, preferably 0.2 to 3% by weight, of condensation products according to the invention, based on the respective ointment, cream, fatty cream, lotion or the respective gel or powder.

In one embodiment of the present invention, powders or concentrates according to the invention can be comprised in the range from 1 to 75% by weight, preferably 10 to 65% by weight of condensation product according to the invention, based on the respective powder or concentrate.

Creams according to the invention are customarily oil-in-water emulsions, ointments according to the invention are customarily water-in-oil emulsions. Ointments and creams according to the invention comprise, in addition to preferably purified water, one or more oil components and preferably one or more surface-active substances, for example one or more emulsifiers or protective colloids. Furthermore, ointments and fatty creams according to the invention—like other administration forms of the condensation products according to the invention as well—comprise preservatives such as, for example, sorbic acid.

Suitable oil components are natural and synthetic waxes, natural and synthetic oils such as, for example, nut oil, fish oil, olive oil and polymers such as, for example, polyacrylic acid, polydimethylsiloxane and polymethylphenylsiloxane.

Suitable surface-active substances are, for example, compounds of the general formula (IV)

$$CH_3-(CH_2)_n-X-R^3 \quad (IV)$$

where the variables are defined as follows:
n is an integer in the range from 0 to 20, is preferably an even number in the range from 2 to 16, and
X is divalent groups which carry at least one atom other than carbon and hydrogen, preferably nitrogen and particularly preferably oxygen, in particular —O— and —COO—, $R^3$ is selected from
hydrogen,
$C_1$-$C_{10}$-alkyl groups such as, for example, methyl, ethyl, n-propyl, isopropyl, n-butyl, iso-butyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl; particularly preferably $C_1$-$C_4$-alkyl such as methyl, ethyl, n-propyl, isopropyl, n-butyl, isobutyl, sec-butyl and tert-butyl,
—$(CH_2-CH_2-O)_m$—H, where m is an integer in the range from 1 to 100, preferably to 25,
$CH_3-(CH_2)_n-X-(O-CH_2-CH_2)_m$—, where X and n can in each case be different or preferably identical.

Furthermore, ointments and creams according to the invention—like other administration forms of the condensation products according to the invention as well—can comprise organic solvents such as, for example, propylene glycol and glycerol.

Preferred examples of surface-active substances are, for example, isopropyl tetradecanoate, cetyl alcohol, palmitic acid, stearic acid, polyoxyethylene 2-stearyl ether, α-n-dodecyl-ω-hydroxypolyoxyethylene having, on average, 10 ethylene oxide units, 2-phenoxyethanol, polyoxyethylene 21-stearyl ether.

Fatty creams according to the invention are customarily water-in-oil emulsions and comprise, in addition to preferably purified water, one or more oil components and preferably one or more surface-active substances, for example one or more emulsifiers or protective colloids.

Suitable oil components are, in addition to the oil components described above, natural and synthetic fats such as, for example, mono- or polyethylenically unsaturated fatty acid glycerides.

Furthermore, fatty creams according to the invention can comprise one or more of the following substances: methyl 4-hydroxybenzoate, propyl 4-hydroxybenzoate, aqueous sorbitol solution, tris[n-dodecylpoly(oxoethylene)-4]phosphate, cetylstearyl alcohol, hexyl laurate, vitamin F glycerol ester, dimethicone 350, calcium lactate pentahydrate.

Gels according to the invention can comprise, for example, polyacrylic acid, sodium hydroxide and butylhydroxyanisole, for example 4-methoxy-2-tert-butylphenol, 4-methoxy-3-tert-butylphenol and mixtures of the two aforementioned compounds.

Lotions according to the invention can comprise, for example, at least one of the substances mentioned below: glycerol, zinc oxide, talc, lecithin, highly disperse silica, isopropanol, methyl 4-hydroxybenzoate, carageenan, sodium salt and phosphoric acid esters of the general formula (V)

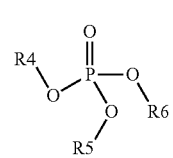

(V)

in which $R^4$, $R^5$ and $R^6$ can be identical or different and are chosen from n-$C_{10}$-$C_{20}$-alkyl, in particular n-$C_{16}$-$C_{18}$-alkyl and H—(O—$CH_2$—$CH_2)_m$, where m is defined as above.

Cosmetic powders according to the invention can comprise, for example: calcium lactate pentahydrate, talc, cornstarch, 2-n-octyl-1-dodecanol, silica.

Powders according to the invention for the preparation of working solutions can comprise, for example, calcium lactate 5 H$_2$O and sodium sulfate (as a carrier material).

Concentrates according to the invention for the preparation of working solutions can comprise, for example: sodium salt of dodecylpoly(oxyethylene)2-hydrogensulfate, sodium sulfate as a carrier material.

Instead of investigating ointments, creams, fatty creams, gels, lotions, cosmetic powders, powders or concentrates according to the invention for their efficacy, condensation products according to the invention, if appropriate as a stock solution, can be investigated for their efficacy. Suitable investigation methods are investigations on the inhibition of selected enzymes, for example human leucocyte elastase or protease plasmin. Furthermore, it can be investigated to what extent the replication of viruses in question is inhibited. Investigation methods of this type are described even more accurately in the following text (pharmacological investigations).

A further subject of the present invention is the use of a condensation product according to the invention for disinfection, as a disinfectant or constituent of a disinfectant. In particular, the condensation products according to the invention are used in the hospital field, in particular hospital intensive care units, toilets, washrooms, households, food production or in stables or cages of animals, in particular of birds, pigs and cattle.

The condensation products according to the invention are distinguished in their use as disinfectants in that they have a surprisingly good broad-spectrum action against fungi, bacteria and viruses, and a lower toxicity toward the customary compositions or mixtures which are used as disinfectants according to the prior art. Furthermore, they are neither volatile nor irritating to the mucous membranes and they can be prepared easily either as a liquid or alternatively scatterable powder adjustment. In particular, the condensation products according to the invention are suitable for use in stables or cages of animals, preferably on straw.

A further subject of the present invention is thus also a disinfectant comprising at least one condensation product according to the invention obtainable by reaction of a1) at least one bicyclic or polycyclic aromatic or heteroaromatic, where the bicyclic or polycyclic aromatic or heteroaromatic is substituted by at least one carboxyl group (—COOH), and where the carboxyl group can be present in salt form, a2) at least one carbonyl compound, a3) if appropriate at least one sulfonating agent a4) at least one urea derivative, and a5) if appropriate at least one further aromatic or heteroaromatic, or a physiologically tolerable salt thereof.

The disinfectants according to the invention are thus not intended for administration as drugs, but they are suitable for the disinfection of, for example, the articles mentioned above. In the disinfectants according to the invention, at least one condensation product according to the invention is contained in the customary concentrations. Further components which are comprised in the disinfectants according to the invention are known to the person skilled in the art. Components of this type can vary, depending on the application area; the same applies for the concentration in the condensation product according to the invention.

A further subject of the present invention is the use of the condensation products according to the invention as a tanning agent or as a tanning aid. Preferably, the condensation products according to the invention are suitable for the tanning of leathers and/or hides. Processes for tanning (tanning processes) as such are known to the person skilled in the art, she, for example, EP-A 0 301 406.

The invention will be illustrated by the following examples.

EXAMPLES

General Information ppm always relates to parts by weight, if not stated otherwise.

The molecular weight determinations are carried out using gel permeation chromatography (GPC):

Stationary phase: poly-(2-hydroxymethacrylate) gel, commercially obtainable as HEMA BIO from PSS, Mainz, Germany, crosslinked with ethylene glycol dimethacrylate.

Eluent: mixture of 30% by weight of tetrahydrofuran (THF), 10% by weight of acrylonitrile, 60% by weight of 1-molar NaNO$_3$ solution Internal standard: 0.001% by weight of benzophenone, based on eluent Flow: 1.5 ml/min Concentration: 1% by weight in the eluent containing internal standard Detection: UVN is spectrometrically at 254 nm Calibration using a polystyrene calibration part from PSS.

$M_n$: number average molecular weight in [g/mol]

$M_w$: weight average molecular weight in [g/mol]

1. Synthesis Examples of Reaction Mixtures

Example 1

Reactants (Starting Materials):

a) phenol, b) concentrated sulfuric acid, c) urea d) formaldehyde e) 1-naphthalenecarboxylic acid Procedure:

47.1 g of phenol are initially introduced into a stirring apparatus and treated for 25 minutes with 57.1 g of concentrated sulfuric acid (96% by weight). Care is taken here that the temperature does not rise above 105° C. Subsequently, the reaction mixture is stirred for 2 hours at 100 to 105° C. The reaction mixture is then diluted with 7.9 g of water. 64.6 g of aqueous urea solution (50% by weight) are metered in, the temperature rising to 95° C.; subsequently the mixture is cooled to 75° C. 94.6 g of aqueous formaldehyde solution (30% by weight) are added over a period of 90 minutes, care being taken that the temperature does not rise above 75° C. Subsequently, the mixture is partially neutralized with 17.3 g of aqueous sodium hydroxide solution (50% by weight), and 6.9 g of water are added. 57.2 g of 1-naphthalenecarboxylic acid and 0.6 g of a complexing agent based on ethylenediaminetetraacetic acid are added at a temperature of 50 to 55° C. The reaction mixture is then stirred for 30 minutes at 55° C., before 26.3 g of aqueous formaldehyde solution (30% by weight) are metered in at 55 to 60° C. in the course of 15 to 20 minutes. 74.4 g of aqueous sodium hydroxide solution (50% by weight) and 46.2 g of water are added. After evaporation of the volatile portions, 152.5 g of condensation product 1 are obtained as a solid having a white color.

The analysis of the reaction mixture 1 by HPLC affords the following values:

phenol: <0.1% by weight;

4-phenolsulfonic acid: 9.8% by weight;

free formaldehyde: <20 ppm;

$M_n$ 2390 g/mol, $M_w$ 35630 g/mol, determined by GPC.

Example 2

Reactants:
a) phenol,
b) concentrated sulfuric acid,
c) urea,
d) formaldehyde,
e) 1-naphthalenecarboxylic acid Procedure:
47.1 g of phenol are initially introduced into a stirring apparatus and admixed with 57.1 g of concentrated sulfuric acid (96% by weight) for 25 minutes. Care is taken here that the temperature does not rise above 105° C. Subsequently, the reaction mixture is stirred for 2 hours at 100 to 105° C. The reaction mixture is then diluted with 8 g of water. 64.6 g of aqueous urea solution (50% by weight) are metered in, the temperature rising to 95° C.; subsequently, the mixture is cooled to 75° C. 141.9 g of aqueous formaldehyde solution (30% by weight) are added over a period of 90 minutes, care being taken that the temperature does not rise above 75° C. Subsequently, the mixture is partially neutralized with 17.3 g of aqueous sodium hydroxide solution (50% by weight), and 10 g of water are added. 57.2 g of 1-naphthalenecarboxylic acid and 0.6 g of a complexing agent based on ethylenediaminetetraacetic acid are added at a temperature of 50 to 55° C. The reaction mixture is then stirred for 30 minutes at 55° C., before 26.3 g of aqueous formaldehyde solution (30% by weight) are metered in at 55 to 60° C. in the course of 15 to 20 minutes. Aqueous sodium hydroxide solution (50% by weight) and 100 g of water are added until a pH of 7.2 is obtained. After evaporation of the volatile portions, condensation product 2 is obtained.

Example 3

Reactants:
a) 1-naphthalenecarboxylic acid,
b) urea,
c) formaldehyde,

Procedure:
47.7 g of 1-naphthalenecarboxylic acid are dissolved in a stirring apparatus in 250 g of water and 22.5 g of aqueous sodium peroxide solution (50% by weight). Care is taken here that the pH of this aqueous solution does not rise above 9. 64.6 g of aqueous urea solution (50% by weight) are metered in at 70° C. the temperature rising to 95° C.; subsequently, the mixture is cooled to 75° C. 94.6 g of aqueous formaldehyde solution (30% by weight) are added over a period of 90 minutes, care being taken that the temperature does not rise above 75° C. 57.2 g of 1-naphthalenecarboxylic acid and 0.6 g of a complexing agent based on ethylenediaminetetraacetic acid are added at a temperature of 50 to 55° C. The reaction mixture is then stirred for 30 minutes at 55° C., before 26.3 g of aqueous formaldehyde solution (30% by weight) are metered in at 8° C. in the course of 15 to 20 minutes. 26.5 g of aqueous sodium hydroxide solution (50% by weight). After evaporation of the volatile portions, 158.2 g of condensation product 3 are obtained as a powder having a white color.

Comparative Example 4

Reactants:
a) phenol,
b) concentrated sulfuric acid,
c) urea,
d) formaldehyde,
d) naphthalenesulfonic acid Procedure:
47.1 g of penol are initially introduced into a stirring apparatus and admixed with 57.1 g of concentrated sulfuric acid (96% by weight) for 25 minutes. Care is taken here that the temperature does not rise above 105° C. Subsequently, the reaction mixture is stirred for 2 hours at 100 to 105° C. The reaction mixture is then diluted with 7.9 g of water. 64.6 g of aqueous urea solution (50% by weight) are metered in, the temperature rising to 95° C.; subsequently, the mixture is cooled to 75° C. 94.6 g of aqueous formaldehyde solution (30% by weight) are added over a period of 90 minutes, care being taken that the temperature does not rise above 75° C. 69.3 g of napthahlene sulfonic acid and 0.6 g of a complexing agent based on ethylenediamine-tetraacetic acid are added at a temperature of 50 to 55° C. The reaction mixture is then stirred for 30 minutes at 55° C., before 26.3 g of aqueous formaldehyde solution (30% by weight) are metered in at 55 to 60° C. in the course of 15 to 20 minutes. Aqueous sodium hydroxide solution (50% by weight) are added until a pH of 7.2 is obtained. After evaporation of the volatile portions, condensation product 4 is obtained.

Comparative Example 5

Reactants:
a) phenol,
b) concentrated sulfuric acid,
c) formaldehyde,
d) 1-naphthalenecarboxylic acid Procedure:
47.1 g of phenol are initially introduced into a stirring apparatus and admixed with 57.1 g of concentrated sulfuric acid (96% by weight) for 25 minutes. Care is taken here that the temperature does not rise above 105° C. Subsequently, the reaction mixture is stirred for 2 hours at 100 to 105° C. The reaction mixture is then diluted with 7.9 g of water. 94.6 g of aqueous formaldehyde solution (30% by weight) are added over a period of 90 minutes, care being taken that the temperature does not rise above 75° C. 57.2 g of 1-naphthalenecarboxylic acid and 0.6 g of a complexing agent based on ethylenediaminetetraacetic acid are added at a temperature of 50 to 55° C. The reaction mixture is then stirred for 30 minutes at 55° C., before 26.3 g of aqueous formaldehyde solution (30% by weight) are metered in at 55 to 60° C. in the course of 15 to 20 minutes. Aqueous sodium hydroxide solution (50% by weight) are added until a pH of 7.2 is obtained. After evaporation of the volatile portions, condensation product 5 is obtained.

Comparative Example 6

Reactants:
a) phenol,
b) concentrated sulfuric acid,
c) urea
d) formaldehyde

Procedure:
20.4 g of phenol are initially introduced into a stirring apparatus and treated for 25 minutes with 24.7 g of concentrated sulfuric acid (96% by weight). Care is taken here that the temperature does not rise above 105° C. Subsequently, the reaction mixture is stirred for 2 hours at 100 to 105° C. The reaction mixture is then diluted with 3.4 g of water. 28.1 g of aqueous urea solution (50% by weight) are metered in, the temperature rising to 95° C.; subsequently the mixture is cooled to 75° C. 41.0 g of aqueous formaldehyde solution (30% by weight) are added over a period of 90 minutes, care being taken that the temperature does not rise above 75° C. Subsequently, the mixture is partially neutralized with 7.5 g of aqueous sodium hydroxide solution (50% by weight), and 3 g of water are added.

13.6 g of phenol and 0.3 g of a complexing agent based on ethylenediaminetetraacetic acid are added at a temperature of 50 to 55° C. The reaction mixture is then stirred for 30 minutes at 55° C., before metering in 11.4 g of aqueous formaldehyde solution (30% by weight) in the course of 15 to 20 minutes at 55 to 60° C. 32.2 g of aqueous sodium hydroxide solution (50% by weight) and 20 g of water are added. The final adjustment of the pH to pH 7.0-7.4 is carried out by addition of 8.2 g of sulfuric acid (50% by weight). After evaporation of the volatile portions, 200 g of reaction mixture 6 are obtained as a colorless solid.

The analysis of the condensation product 6 affords the following values:
phenol by HPLC: <0.1% by weight;
4-phenolsulfonic acid by HPLC: 7.8% by weight;
free formaldehyde: <20 ppm;

2. Pharmacological Investigations

Process for the Determination of the Antiviral Activity

In the investigation, it is determined whether a condensation product has antiviral activity against various viruses and what amount of antiviral substance is needed in order to bring about a 50% reduction of virus replication.

The virus working dilution is determined with the aid of an endpoint titration of the cultured virus isolate. In this titration, the amount of a virus is determined at which 50% of the batches from the virus dilution are infected or not infected (=infectious dose 50%=$TCID_{50}$/ml).

A dilution series increasing by a factor of two is prepared from the substance to be tested. A defined amount of virus is then added.

The substance/virus mixture is added to monolayers of suitable cells. After an incubation period dependent on the virus, an assessment of the virus-related cytopathogenic effect (CPE) is carried out. For the determination of the results, staining by means of antibodies against the virus employed follows. Here, a percentage estimate of the CPE takes place in comparison to the virus control, which is set at 100%. On staining, a photometric evaluation is carried out. By means of linear regression using a computer program, the concentration at which a 50% reduction of virus replication of patient isolates is induced ("$IC_{50}$") is calculated.

The concentration of condensation product which reduces the cell viability by 50% is called "$TC_{50}$" (=toxic concentration). $TC_{50}$ indicates the toxic effects of the reaction mixture.

The $TC_{50}/IC_{50}$ ratio (called the therapeutic index "TI") shows the specific activity of a condensation product against a given virus.

Endpoint Titration of the Virus
  Preparation and Distribution of the Cell Suspensions
  1. General
    about 100 ml of cell suspension can be prepared from a Vero cell culture bottle (75 $cm^2$, about. $9 \times 10^6$ cells) having a confluent cell lawn.
    5 ml of cell suspension are needed per microtiter plate
  2. Preparation of the Cell Suspensions
    the cell culture is trypsinized, homogenized and transferred to growth medium
  3. Distribution of the Cell Suspension
    prepare 50 µl of cell suspension per well
    then store plates in the incubator until further use Titration of the Viruses
  preparation of a 1:10 dilution series
    in each case pipette 50 µl of dilution per well in the 8-fold batch into a plate prepared with cell suspension
  depending on the virus, incubate the plate in the incubator for a few days
  after the incubation period, assess plates microscopically for CPE Test Preparation for the Determination of the Antiviral Activity
  Per virus to be investigated, a 96-well plate containing appropriate cells must be prepared
  Labeling of the plates.
    1st row CC (cell control)
    2nd row VC (virus control)
    3rd-10th rows substance concentrations
    on the edge virus and date Test Procedure
  using the substance to be tested prepare a 1:2 dilution series
  In row 1 of the plate add 100 µl of medium to the cells (no substance and virus dilution)
  In row 2 pipette 50 µl of medium (no substance dilution)
  Distribute the substance dilution of rows 3-12 in the 8-fold batch onto the plate
  Carry out the pipetting into the plates rapidly, as otherwise the cells will dry out
    prepare an adequate amount of virus suspension for, usually, MOI 0.01
    pipette 50 µl of virus suspension from row 2
    incubate plate at 37° C. in the $CO_2$ incubator for 2 days Test Evaluation
  After the end of the incubation period evaluate the plate microscopically for CPE. The virus control corresponds to 100% here. By comparison with the virus control, the extent of cell destruction is indicated as a percentage for all substance dilutions. After visual evaluation, staining can follow.

Staining with Virus-Specific Antibodies
  under the sterile safety cabinet, aspirate supernatant from microtiter plates
  fixation of the cells using acetone/methanol
  aspirate liquid
  dilution of the virus-specific antibodies with blocking solution. 50 µl are employed per cavity. The optimum concentration for the antibody is determined for each new batch by means of titration. Incubation for 1 h at 37° C.
  3× washing with wash buffer
  biotinylated anti-IgG antibodies are diluted in wash buffer and 50 µl each are pipetted into each cavity. The optimum concentration for the antibody is determined for each new batch by means of titration.
  incubation for 1 h 37° C.
  3× washing
  the streptavidin/peroxidase conjugate is diluted in the wash buffer and 50 µl per cavity are employed. The optimum concentration of the conjugate is determined for each new batch by means of titration.
  incubation for 30 min at 37° C.
  3× washing
  50 µl of substrate solution are pipetted into each cavity
  when using a soluble substrate, pipette 2 rows containing 50 µl on a separate plate (=substrate blank value)
  incubation for 10 min at RT
  add 100 ml of 1N sulfuric acid for stopping in the case of a soluble substrate
  analysis photometrically at a wavelength of 450 nm and a reference wavelength of 630 nm the analysis should be carried out within one hour after the end of the test
Criteria for the Analytical Release of the Results:
the cell control must show a confluent, morphologically inconspicuous cell lawn
the virus control is set as 100% CPE
in the calculation of the $IC_{50}$ value, "r" must not be smaller than 0.90
Evaluation and Documentation
Visual Evaluation
in the case of visual evaluation, the magnitude of the CPE or of the staining in comparison with the virus control is read off and recorded as a % value
here, the CC must have a confluent cell lawn
in principle, appraise all wells
Photometric Evaluation
in the case of photometric evaluation, a mean value is in each case calculated from all 8-fold determinations
the mean value of the substrate blank values is subtracted from all calculated mean values
the OD value of the VC corresponds to 100%
the % values of the substance dilutions employed are calculated by means of rule of three
Calculation of the $IC_{50}$ Value
determine the respective mean value from the 8 individual values of the controls or of the substance determinations
subtract the substrate blank value from all values
in the antiviral determination, the value of the VC corresponds to 100%
calculate the % value in relation to the respective control for the individual values of the substance determinations
employ determined % values in the computer program Calcusyn for Windows (Biosoft) and calculate the $IC_{50}$ value.
Quality Control
A substance having known antiviral activity compared to the test virus is comprised in each batch. A cell and virus control is comprised in each batch.
Examples of Antiviral Activity of Condensation Products
Condensation Product from Example 1

| Virus | $IC_{50}$ (µg/ml) | $TC_{50}$ (µg/ml) | TI |
|---|---|---|---|
| Herpes simplex virus 1 (HSV-1) | 1.7 | 1670 | 982 |
| Herpes simplex virus 2 (HSV-2) | 0.9 | 1670 | 1856 |
| HCMV | 0.3 | 1670 | 5567 |
| Human immunodeficiency virus type 1 (HIV-1) | 0.7 | 305 | 436 |

Condensation Product from Example 2

| Virus | $IC_{50}$ (µg/ml) | $TC_{50}$ (µg/ml) | TI |
|---|---|---|---|
| Herpes simplex virus 1 (HSV-1) | 0.89 | 872 | 980 |
| Herpes simplex virus 2 (HSV-2) | 0.77 | 872 | 1132 |
| HCMV | 0.33 | 872 | 2642 |

Condensation Product from Example 3

| Virus | $IC_{50}$ (µg/ml) | $TC_{50}$ (µg/ml) | TI |
|---|---|---|---|
| Herpes simplex virus 1 (HSV-1) | 2500 | 500 | 0.2 |
| Herpes simplex virus 2 (HSV-2) | 1500 | 500 | 0.3 |

Condensation Product from Comparative Example 4

| Virus | $IC_{50}$ (µg/ml) | $TC_{50}$ (µg/ml) | TI |
|---|---|---|---|
| Herpes simplex virus 1 (HSV-1) | 1.34 | 885 | 660 |
| Herpes simplex virus 2 (HSV-2) | 0.87 | 885 | 1017 |
| HCMV | 0.42 | 885 | 2107 |

Condensation Product from Comparative Example 5

| Virus | $IC_{50}$ (µg/ml) | $TC_{50}$ (µg/ml) | TI |
|---|---|---|---|
| Herpes simplex virus 1 (HSV-1) | 2.85 | 632 | 220 |
| Herpes simplex virus 2 (HSV-2) | 2.40 | 632 | 263 |
| HCMV | 1.88 | 632 | 336 |

Condensation Product from Comparative Example 6

| Virus | $IC_{50}$ (µg/ml) | $TC_{50}$ (µg/ml) | TI |
|---|---|---|---|
| Herpes simplex virus 1 (HSV-1) | 10.4 | 99.2 | 9.5 |
| HCMV | 1.59 | 99.2 | 62.39 |
| Human immunodeficiency virus type 1 (HIV-1) | 10.8 | 405 | 37.7 |

The comparison of example 1 and comparative example 6 shows that the condensation products according to the invention have a decreased $IC_{50}$ value and a markedly higher $TC_{50}$ value and thus also a markedly improved TI index for the HSV-1 virus than the condensation products known from the prior art. The condensation product 3 according to the invention shows a markedly higher $TC_{50}$ value for the HSV-1 virus than comparative example 6, in which no component a1) is comprised as starting material (reactant) of the condensation product. The condensation products according to the invention thus show improved pharmaceutical efficacy.

Inhibition of the Enzyme Human Leucocyte Elastase (HLE)

To demonstrate a change in enzyme activity, HLE is incubated together with the synthetic substrate N-methoxysuccinyl-Ala-Ala-Pro-Val-pNitro-Anilid (AAPV). The conversion of AAPV is determined photometrically at 405 nm.

The condensation products from the examples are added to the batch in different concentrations. A dose-dependent inhibition of the HLE activity is found for the condensation products of example 1 and comparative example 6. The half maximum effective concentration ($EC_{50}$) is 0.3 µg/ml for example 1 and 0.4 µg/ml for comparative example 6.

Effect of Condensation Products in an Animal Model of Chronic Obstructive Pulmonary Disease (COPD)

To investigate the effect of example 1 in a model of chronic obstructive pulmonary disease (COPD), male Syrian golden hamsters (mean weight 125 g±6 g) are divided into two groups (active drug group and control group) of 10 hamsters each. The animals of the two groups are anesthetized by means of intraperitoneally administered ketamine (95 mg/kg) and xylazine (17 mg/kg) and subsequently endotracheally intubated. The active drug group receives 250 µl of a solution (0.5 µg/ml) of example 1 endotracheally into the bronchial system, while 250 µl of isotonic sodium chloride solution are administered to the control group. After 30 minutes, both groups receive a second instillation with 100 µl of human leucocyte elastase (HLE, 500 µg/ml in sterile 0.9% NaCl solution). After 4 hours (6 animals per group) and after 24 hours (4 animals per group) after the last instillation, the animals are killed (Phenobarbital 70 mg/kg intraperitoneally). A broncho-alveolar lavage (BAL) is carried out for the animals killed 4 hours after the instillation. For the BAL, 2.5 ml of 0.9% NaCl solution is used repeatedly (altogether 3 times) and then the hemoglobin concentration in the instillate is determined spectrophotometrically. This value is used as a measure of the damage to the lungs by hemorrhagia due to HLE.

Effect of Aerosols of the Condensation Products in an Animal Model of COPD (I)

Male Syrian golden hamsters (mean weight 105 g±8 g) are divided into two groups (active drug group and control group) of 6 hamsters each. The animals of the two groups are initially anesthetized intraperitoneally (ketamine 95 mg/kg, and xylazine 17 mg/kg) and subsequently endotracheally intubated by means of direct laryngoscopy. Both groups receive 100 µl of HLE (500 µg/ml in sterile 0.9% NaCl solution). The animals are then treated in separate cages with a continuous treatment with an aerosol of example 1 (5 µg/ml) (active drug group) or isotonic sodium chloride solution (control group) in the respiratory air (relative humidity 60%) for 24 hours. After this treatment, the animals are killed (Phenobarbital 70 mg/kg intraperitoneally) and a broncho-alveolar lavage (BAL) is carried out. For the BAL, 2.5 ml of 0.9% NaCl solution is instilled repeatedly (altogether 3 times) and then the hemoglobin concentration in the instillate is determined spectrophotometrically. This value is used as a measure of the damage to the lungs by hemorrhagia due to the serine protease (HNE).

Effect of Aerosols of the Condensation Products in an Animal Model of COPD (II)

Male Syrian golden hamsters (mean weight 115 g±10 g) are used for these experiments. The animals are initially anesthetized intraperitoneally (ketamine 95 mg/kg, and xylazine 17 mg/kg) and subsequently endotracheally intubated All the animals receive 100 µl of human leucocyte elastase (500 µg/ml in sterile 0.9% NaCl solution by endotracheal instillation. 4 animals are then placed in separate cages (2 hamsters in each cage) and are subjected to a continuous treatment with an aerosol of example 1 (concentration of the condensation products of example 1 is 5 µg/ml) or water-aerosol in the respiratory air (relative humidity 60%) for 4 hours. After this treatment, all the animals are killed (Phenobarbital 70 mg/kg intraperitoneally) and a broncho alveolar lavage (BAL) is carried out. For the BAL, 2.5 ml of 0.9% NaCl solution is used repeatedly (altogether 3 times) and then the hemoglobin concentration in the instillate is determined spectrophotometrically. This value is used as a measure of the damage to the lungs by hemorrhagia due to the HLE.

Effect of Condensation Products in a Model for Myocardial Reperfusion Injury

The reperfusion injury is brought about in male white New Zealand rabbits through a hypoperfusion of the myocardial tissue as a result of ligating a coronary artery (Bidouard J P et al., Eur J Pharmacol. 2003;461:49-52). By thorocotomy, a side branch of the left coronary artery is occluded by ligature for 30 minutes and subsequently reopened to achieve a reperfusion for 120 minutes. Before removal of the heart, colored ink is introduced into the ascending aorta. To investigate the effect of example 1 on the reperfusion injury, the animals are divided into 3 groups with 3 animals in each. An intravenous treatment with example 1 (5 µg/ml in isotonic sodium chloride solution) is administered to group 1 15 minutes before and to group 2 25 minutes after the reopening of the coronary artery, while a third group (the control group) is treated with isotonic sodium chloride solution alone.

The animals are killed, and the hearts are removed, fixed with formalin and embedded in paraffin. By means of appropriate sections, the heart is examined for the distribution of the ink. In addition, neutrophil granulocytes containing the HLE enzyme are depicted in histological section by means of alpha-naphthol chloroacetate esterase staining.

Inhibition of Ischemic Injury in the Brain by the Condensation Product

The effect of example 1 on cerebral ischemic injury is investigated in an animal model. Adult Long-Evans rats receive a cerebral ischemia by occlusion of both carotid arteries for one hour, followed by a 24 hour reperfusion after reopening of the vessels. The severity of the injury is evaluated according to neuro-vegetative symptoms (spontaneous activity, coordinated walking, forward stretching and climbing). The injury to the brain tissue is likewise studied histologically. The animals in two experimental groups of 3 rats each are infused either with example 1 (5 µg/ml in isotonic sodium chloride solution) (active drug group) or with isotonic sodium chloride solution alone (control group) 15 minutes before initiation of the ischemia and immediately before the subsequent reperfusion.

Effect of Condensation Products in Bullous Pemphigoid

Blister fluid is taken from patients with bullous pemphigoid and used for an ex vivo model (Verraes et al., J Invest Dermatol. 2001; 117:1091-6). Recombinant, radioactively labeled BP180 antigen, the target antigen with this disorder, is subsequently added to the blister fluid and the degradation is determined autoradiographically following gel electrophoresis. To inhibit the elastase activity in the blister fluid, either example 1 (5 µg/ml) or the elastase inhibitor chloromethyl ketone is added. An untreated control is used for comparison.

Effect of Condensation Products in Psoriasis Vulgaris

Psoriasis is characterized by detection of neutrophil granulocytes in the uppermost skin layers. High activity of HLE can be detected on the lesional skin (Wiedow et al., J Invest Dermatol. 1992; 99:306-9).

To determine the effect of example 1 in psoriasis vulgaris, a half side experiment is carried out. To this end, example 1 is used in a concentration of 50 µg/mg in DAC base cream. Patients are included which have comparable lesions on the two elbows. Evaluation is in terms of the local psoriasis severity index (LPSI) (Henneicke-von Zepelin et al., Br J Dermatol. 1993; 129:713-7). The patients are instructed to apply the contents of the tubes marked "right" and "left" 2 times/day to the corresponding lesions. One tube contains the example 1-containing cream, the other the DAC base cream without addition. Allocation is random. The LPSI is determined every 2 weeks.

Effect of Condensation Products in Peritonitis and Septic Shock

In an infectious peritonitis animal model, the effect of example 1 in a peritoneal dialysis is investigated (Welten et al., Nephrol Dial Transplant. 2004; 19:831-9.). To this end, male Wistar rats were fitted with a catheter for peritoneal dialysis, which is used to induce a peritonitis and for further peritoneal dialysis. A purulent peritonitis is produced by infusion of a suspension of S. aureus ATCC 25923 ($1 \times 10^9$ c.f.u in 0.5 ml). After 4 hours, a peritoneal lavage is carried out either with isotonic sodium chloride solution or with an isotonic sodium chloride solution containing 5 µg/ml of example 1. After the death of the animals, but at the latest after 24 hours, the bacterial colonization and also the inflammatory reaction in the peritoneum is investigated histologically.

Effect of Condensation Products on Allergenic Potency of Type 1 Allergens

An extract of the house dust mite *Dermatophagoides pteronissinus* (*D. pter*) is treated with example 1 (final concentration 50 μg/ml). Subsequently, the *D. pter*/example 1 extract is tested in a prick test on patients who gave a positive reaction to the conventional test fluid with *D. pter*. The control used was again the untreated test solution, histamine solution 0.1%, histamine solution treated with example 1, and also isotonic sodium chloride solution.

Effect of a Cotton Cloth Coated with Condensation Products on Nocturnal Symptoms of Patients with Proven Type 1 Sensitization to House Dust Mites (*D. pteronissinus*)

Mattresses represent a significant source of house dust mite allergies of the immediate type (type 1 allergy). The affected patients have nocturnal sneezing attacks, teary eyes and a runny nose. Allergen-impervious mattress covers are frequently used for prophylaxis.

In an experiment, closely woven cotton fabric is given an example 1-containing coating. The study includes 10 patients each with proven type 1 sensitization to *D. pter* (prick test; detection of specific IgE, at least CAP class 3). They receive, on a randomized basis, mattress covers coated with example 1 or untreated mattress covers. The effect is documented by means of a standardized patient diary, recording frequency of waking up during the night, the number of sneezing attacks and, by means of visual analog scales, the severity of the running nose and teary eye symptoms.

Effect of Condensation Product-Containing Nose Spray in Patients with Allergic Rhinitis In a test, patients with proven allergic rhinitis to grass pollen receive either a nose spray containing 50 μg/ml of example 1 or isotonic sodium chloride solution. 5 patients per group are instructed to use the spray 6 times/day.

Effect of Condensation Product-Containing Eye Drops in Patients with Allergic Conjunctivitis In a test, patients with proven allergic conjunctivitis receive either eye drops containing 5 μg/ml of example 1 or isotonic sodium chloride solution. 5 patients per group are instructed to use the drops 6 times/day.

Effect of Condensation Product-Containing Aerosol in Allergic Bronchial Asthma

Ten-week-old Brown Norway rats were used to test the effect of example 1 (Roumestan et al., Resp Res 8:35-46, 2007). The animals were sensitized by repeated intraperitoneal injections of ovalbumin. The animals were then transferred into a conditioned cage and constantly treated for 6 days with an aerosol of isotonic sodium chloride solution or example 1 solution. This was followed by asthma triggering with an ovalbumin-containing aerosol. Effectiveness is measured by determining the change in the resistance to air flow by barometric plethysmography on the living animals after 24 h.

Application of Condensation Product Infusions in Systemic Vasculitides as Exemplified by Wegener's Granulomatosis.

In Wegener's granulomatosis, neutrophil granulocytes become activated and hence have an important significance for the pathogenesis of WG. Disease activity can be determined by determining levels of proteinase 3-antineutrophil cytoplasmatic antibodies (PR3-ANCA).

In an open study with WG patients the effect of an infusion of example 1 once daily for a week in addition to individual systemic therapy was investigated for 5 patients. The assay of the PR3-ANCA in the serum before and after one week after the last example 1-containing infusion serves as control parameter. Five patients which only received their individual therapy without further infusions serve as comparison.

The invention claimed is:

1. A condensation product or a physiologically tolerable salt thereof produced by a reaction of a1) 1-naphthalenecarboxylic acid or a salt thereof, a2) at least one aldehyde selected from formaldehyde, acetaldehyde and propionaldehyde a3) concentrated sulfuric acid a4) at least one urea derivative selected from urea, melamine,

I.1

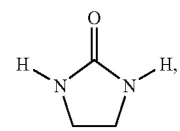

I.2 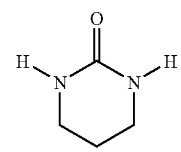 or

I.3 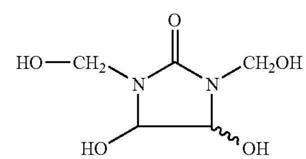 and a5) optionally phenol.

2. The condensation product according to claim 1, wherein the condensation product is present as a mixture with at least one tanning agent.

3. The condensation product according to claim 2, wherein the tanning agent is a synthetic or plant tanning agent.

4. A method for the treatment of genital warts, cancer of the uterine cervix, allergic or nonallergic eczema, diaper rash, pruritus bullous pemphigoid, psoriasis vulgaris, the allergenic potency of type 1 allergens, allergic rhinitis, allergic conjunctivitis, allergic bronchial asthma, psoriasis, inflammatory diseases, autoimmune diseases, rheumatism, melanomatous carcinomas, inflammations of the skin, herpes, chickenpox, AIDS, lung diseases, myocardial reperfusion, ischemic brain damage, peritonitis, septic shock or systemic vasculitides, comprising administering to animals or humans in need thereof an efficacious amount of a condensation product according to claim 1 or a physiologically tolerable salt thereof.

5. A method of claim 4, wherein herpes is a herpes is a herpes labilis or herpes simplex.

6. A method of treating animals or humans in need thereof with an antiviral agent, comprising administering an efficacious amount of a condensation product according to claim 1 or a physiologically tolerable salt thereof.

7. The method of claim 6, wherein the antiviral agent is against endogenous retroviruses, herpes viruses, HCMV viruses, HIV viruses, coronaviruses, flaviviruses, togaviruses or paramyxoviruses.

8. A pharmaceutical composition comprising an efficacious amount of at least one condensation product according to claim 1 and a physiologically tolerable vehicle.

9. The pharmaceutical composition according to claim 1, wherein the pharmaceutical composition is present in the form of a pill, tablet, lozenge, granules, capsule, hard or soft gelatin capsule, aqueous solution, alcoholic solution, oily solution, syrup, emulsion, suspension, suppository, pastille, solution for injection or infusion, ointment, tincture, cream, lotion, cosmetic powder, spray, or a transdermal therapeutic system, nasal spray, aerosol, aerosol mixture, microcapsule, implant, rod, patch or gel or wherein the pharmaceutical composition is a constituent of healthcare products such as sunscreen creams, nasal sprays, mouthwashes, toothpastes, plasters, (wet) wipes, cleansing lotions or shampoos.

10. A method of disinfection employing a condensation product according to claim 1 as a disinfectant or constituent of a disinfectant in the hospital field, toilets, washrooms, households, food production or in stables or cages of animals.

11. A disinfectant comprising the condensation product according to claim 1.

12. A process for the preparation of a condensation product according to claim 1, wherein the individual components a1), a2), a3) and a4) and optionally a5) are reacted with one another in one or in a number of stages.

13. A method of tanning employing a condensation product according to claim 1 as a tanning agent or constituent of a tanning agent to leathers or hides.

* * * * *